United States Patent
Kwon et al.

(10) Patent No.: US 10,364,221 B2
(45) Date of Patent: Jul. 30, 2019

(54) MONOMER, ORGANIC LAYER COMPOSITION, ORGANIC LAYER, AND METHOD OF FORMING PATTERNS

(71) Applicant: SAMSUNG SDI CO., LTD., Yongin-si, Gyeonggi-do (KR)

(72) Inventors: Hyo Young Kwon, Suwon-si (KR); Sunhae Kang, Suwon-si (KR); Ran Namgung, Suwon-si (KR); Younhee Nam, Suwon-si (KR); Yumi Heo, Suwon-si (KR); Young Min Kim, Suwon-si (KR); Soohyoun Mun, Suwon-si (KR)

(73) Assignee: SAMSUNG SDI CO., LTD., Yongin-si, Gyeonggi-do (KR)

( * ) Notice: Subject to any disclaimer, the term of this patent is extended or adjusted under 35 U.S.C. 154(b) by 0 days.

(21) Appl. No.: 15/176,191

(22) Filed: Jun. 8, 2016

(65) Prior Publication Data

US 2017/0008843 A1    Jan. 12, 2017

(30) Foreign Application Priority Data

Jul. 6, 2015 (KR) .................. 10-2015-0095960

(51) Int. Cl.
| | |
|---|---|
| G03F 7/09 | (2006.01) |
| C07D 209/12 | (2006.01) |
| C07D 209/62 | (2006.01) |
| C07D 209/82 | (2006.01) |
| C07D 209/90 | (2006.01) |
| C07D 311/82 | (2006.01) |
| C07D 307/80 | (2006.01) |
| C07D 307/92 | (2006.01) |
| C07D 333/56 | (2006.01) |
| C07D 333/74 | (2006.01) |
| C07D 335/12 | (2006.01) |
| C07D 345/00 | (2006.01) |
| C07D 219/00 | (2006.01) |
| C09D 179/04 | (2006.01) |
| C07D 209/86 | (2006.01) |
| G03F 7/075 | (2006.01) |

(52) U.S. Cl.
CPC ......... *C07D 209/12* (2013.01); *C07D 209/62* (2013.01); *C07D 209/82* (2013.01); *C07D 209/86* (2013.01); *C07D 209/90* (2013.01); *C07D 219/00* (2013.01); *C07D 307/80* (2013.01); *C07D 307/92* (2013.01); *C07D 311/82* (2013.01); *C07D 333/56* (2013.01); *C07D 333/74* (2013.01); *C07D 335/12* (2013.01); *C07D 345/00* (2013.01); *C09D 179/04* (2013.01); *G03F 7/0752* (2013.01); *G03F 7/091* (2013.01); *G03F 7/094* (2013.01)

(58) Field of Classification Search
None
See application file for complete search history.

(56) References Cited

U.S. PATENT DOCUMENTS

| | | | | |
|---|---|---|---|---|
| 3,637,748 A * | 1/1972 | Psaar et al. | .......... | C07D 209/14 544/143 |
| 3,684,510 A * | 8/1972 | Psaar et al. | ............ | G03C 1/675 430/337 |
| 5,217,845 A * | 6/1993 | Steppan | ............... | C07D 219/02 430/273.1 |
| 2006/0142562 A1 | 6/2006 | Lindsey et al. | | |
| 2007/0122740 A1* | 5/2007 | Hatakeyama | ........... | G03F 7/091 430/270.1 |
| 2009/0286188 A1 | 11/2009 | Hatakeyama et al. | | |
| 2011/0117501 A1* | 5/2011 | Song | ...................... | C08G 61/02 430/315 |
| 2011/0155944 A1* | 6/2011 | Cho | ........................ | C07C 33/26 252/62.51 R |
| 2012/0077345 A1* | 3/2012 | Saito | ...................... | C08G 12/26 438/703 |
| 2013/0280913 A1* | 10/2013 | Shinjo | .................. | C09D 139/04 438/694 |
| 2014/0023969 A1* | 1/2014 | Imada | ...................... | C08G 8/08 430/270.1 |
| 2014/0183701 A1* | 7/2014 | Choi | ................. | H01L 21/02118 257/618 |
| 2015/0001178 A1* | 1/2015 | Song | ..................... | C07C 217/58 216/47 |

(Continued)

FOREIGN PATENT DOCUMENTS

| CN | 103910610 A | 7/2014 |
|---|---|---|
| CN | 104024940 A | 9/2014 |

(Continued)

OTHER PUBLICATIONS

Alamgir, "Synthesis and reactivity of some activated heterocyclic compounds", Thesis, 292 pages, (Mar. 2007).*
Black et al., "Synthesis of a new class of indole-containing macrocycles". Chem. Soc., Chem. Comm. 1989 pp. 425-426.*
Somphol et Al. "A new strategy for calixindole formation: synthesis of a calix[3]indole with 2,2; 7,2;7,7-methylene linkages . . . " Synlett vol. 24 pp. 0024-0028 (2013).*
Filatov et al., "A facile and reliable methods for the synthesis of tetrabenzop[orphyrin for 4,7-dihydroisoindole", Eur. J. Chem. Soc., 3468-3475 (2007).*

(Continued)

*Primary Examiner* — Martin J Angebranndt
(74) *Attorney, Agent, or Firm* — Lee & Morse, P.C.

(57) ABSTRACT

A monomer, an organic layer composition, an organic layer, and a method of forming a pattern, the monomer being represented by the following Chemical Formula 1:

[Chemical Formula 1]

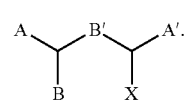

11 Claims, 2 Drawing Sheets

(56) References Cited

U.S. PATENT DOCUMENTS

| | | | | |
|---|---|---|---|---|
| 2015/0011092 A1* | 1/2015 | Someya | ............... | C08G 73/06 438/703 |
| 2015/0044876 A1* | 2/2015 | Nishimaki | ............ | G03F 7/091 438/703 |
| 2015/0194312 A1* | 7/2015 | Someya | ............... | G03F 7/094 438/703 |
| 2015/0315333 A1* | 11/2015 | Han | ..................... | G03F 7/36 430/323 |
| 2016/0147151 A1* | 5/2016 | Shinjo | ................ | C08G 12/26 438/694 |
| 2017/0097568 A1* | 4/2017 | Endo | ..................... | G03F 7/11 |
| 2017/0227850 A1* | 8/2017 | Nishimaki | ............. | G03F 7/11 |

FOREIGN PATENT DOCUMENTS

| | | | | |
|---|---|---|---|---|
| CN | 104250228 A | | 12/2014 | |
| CN | 104749886 A | | 7/2015 | |
| JP | 07-248570 | * | 9/1995 | ............ C09K 9/02 |
| JP | WO2012/077640 A1 | | 6/2012 | |
| JP | 5118073 B2 | | 1/2013 | |
| JP | WO2013/005797 A1 | | 1/2013 | |
| JP | 5641253 B2 | | 12/2014 | |
| KR | 10-0816735 B1 | | 3/2008 | |
| KR | 10-2008-0062963 A | | 7/2008 | |
| KR | 10-2009-0077940 A | | 7/2009 | |
| KR | 10-2010-0072660 A | | 7/2010 | |
| KR | 10-2012-0105370 A | | 9/2012 | |
| KR | 10-2013-0026912 A | | 3/2013 | |
| KR | 2010-080139 | * | 4/2013 | ............ C08G 1/10 |
| KR | 10-2013-0046498 A | | 5/2013 | |
| KR | 10-2014-0122225 A | | 10/2014 | |
| KR | 10-2014-0144207 A | | 12/2014 | |
| KR | 10-2015-0002929 A | | 1/2015 | |
| WO | 2012/005418 | * | 1/2012 | ............... G03F 7/11 |
| WO | WO 2012/077640 A1 | | 6/2012 | |
| WO | WO 2013/005797 A1 | | 1/2013 | |
| WO | WO 2014/208499 A1 | | 12/2014 | |

OTHER PUBLICATIONS

Wen et al., "Fluorinated alcohol-mediated SN1-type reaction of indolyl alcohols with diverse nucleophiles", Adv. Synth. Chem., vol. 357, pp. 4023-4030 (2015).*

Santoso et al., "Some acid catalyzed reactions of indol-3-yl and indol-2-yl disubstituted methanols", Coll. Czech. Chem. Commun. vol. 74 (7-8) pp. 1137-1150 (2009).*

Black et al., "Reaction of 4,6-dimethoxy-3-methylindole with aromatic aldehydes: a simple synthesis of calix[3]indoles", Aust. J. Chem., vol. 49 pp. 311-318 (1996).*

Black et al., "Acid-catalyzed reactions of activated benzofuranylmethanols:formation of calixbenzofurans", Tetrahed., vol. 58 pp. 5125-5134 (2002).*

Brown et al. "Electrophilic substituent constants", JACS 80(18) pp. 4979-4987 (1958).*

Uenishi et al. "Practical entioselective arylation and heteroarylation of aldehydes with in situ prepared organotitanium reagents catalyzed by 3-aryl-H8-BINOL-derived titanium complexes" , Chem., Eur. J., vol. 19 pp. 4896-4906 (2013).*

Bera et al., "Bronstead acid catalyzed [3+2}0 cycloaddition of 2-vinylindoles with in situ generated 2-methide-2H-indoles highly enantioselective synthesis of pyrrolo[1,2]indoles". Chem. Eur., J., vol. 22 pp. 7074-7078 (Mar. 2016).*

Gou et al., "The direct asymmetric alkylation of -amino aldedhydes with 3-indolylmethanols by enamine catalysis". Org. Lett., vol. 16 6472-6475 (Dec. 2014).*

Taiwanese Search Reporet dated Mar. 7, 2017, of corresponding Taiwanese Patent Application No. 105119483.

Motoki Toganoh, et al., "Doubly N-Fused Porphyrin", Angew. Chem. Int. Ed., vol. 47, pp. 8913-8916.

Hongbin Zhao, et al., "Efficient Synthesis of Novel Porphyrin Dimers with Versatile Linkers via Bis(dispyrromethanes) in an Excellent Mixed-Solvent", Aust. J. Chem, vol. 66, pp. 972-982.

* cited by examiner

FIG. 1

$$\Delta mass = \frac{-\Delta freq * A * sqrt(\mu q * pq)}{2(Fq^2)}$$

- $\Delta mass$ = mass change
- $\Delta freq$ = Resonant frequency change
- $\Delta A$ = Area of active surface($0.198 cm^2$)
- $\Delta \mu q$ = AT-cut quartz constant($2.947 \times 10^{11} cm*s^2$)
- $pq$ = Quartz crystal density($2.65 g/cm^3$)
- $Fq$ = Reference frequency($9.00 MHz$)

$$\text{Planarization} = \left(1 - \frac{h_2}{h_1}\right) \times 100$$

MONOMER, ORGANIC LAYER COMPOSITION, ORGANIC LAYER, AND METHOD OF FORMING PATTERNS

CROSS-REFERENCE TO RELATED APPLICATION

Korean Patent Application No. 10-2015-0095960, filed on Jul. 6, 2015, in the Korean Intellectual Property Office, and entitled: "Monomer, Organic Layer Composition, Organic Layer, and Method of Forming Patterns," is incorporated by reference herein in its entirety.

BACKGROUND

1. Field

Embodiments relate to a monomer, an organic layer composition, and a method of forming patterns.

2. Description of the Related Art

Recently, a high integration design in accordance with down-sizing (miniaturization) and complexity of an electronic device has accelerated development of a more advanced material and its related process, and accordingly, lithography using a conventional photoresist may use new patterning materials and technics.

In a patterning process, an organic layer called as a hardmask layer may be formed as a hard interlayer to transfer the fine pattern of the photoresist down to a sufficient depth on a substrate without its collapse.

SUMMARY

Embodiments are directed to a monomer, an organic layer composition, and a method of forming patterns.

The embodiments may be realized by providing a monomer represented by Chemical Formula 1:

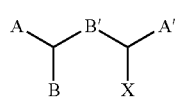

[Chemical Formula 1]

wherein, in Chemical Formula 1, A and A' are each independently a substituted or unsubstituted C6 to C50 cyclic group, B and B' are each independently a substituted or unsubstituted C2 to C50 heterocyclic group, and X is a hydroxy group.

The heterocyclic group may include at least one of N, O, S, Te, and Se.

A and A' may each independently be a substituted or unsubstituted cyclic group of one of the following compounds:

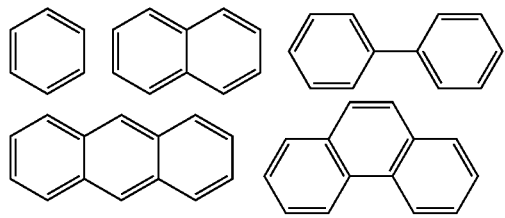

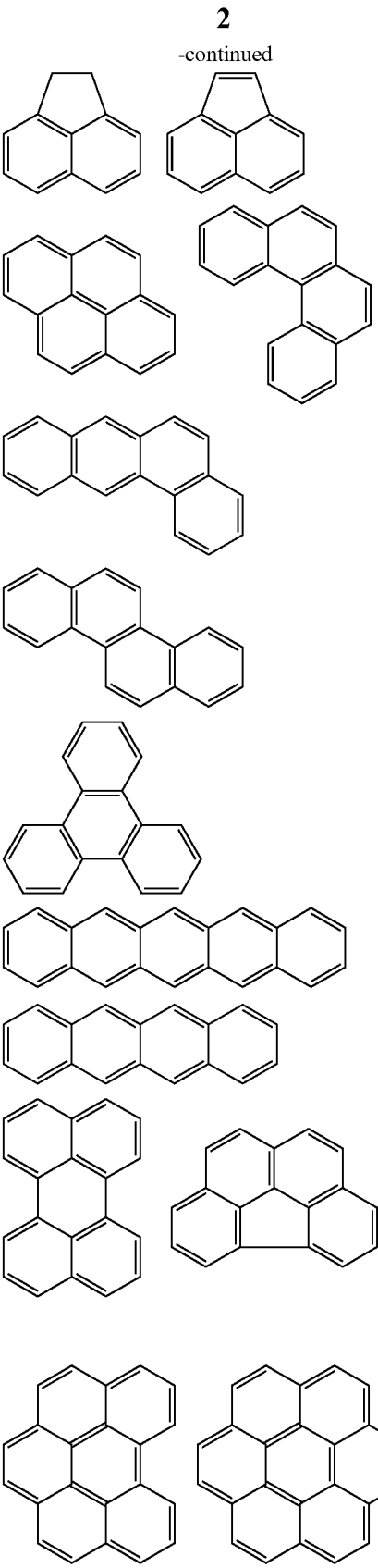

B and B' may each independently be a substituted or unsubstituted heterocyclic group of one of the following compounds:

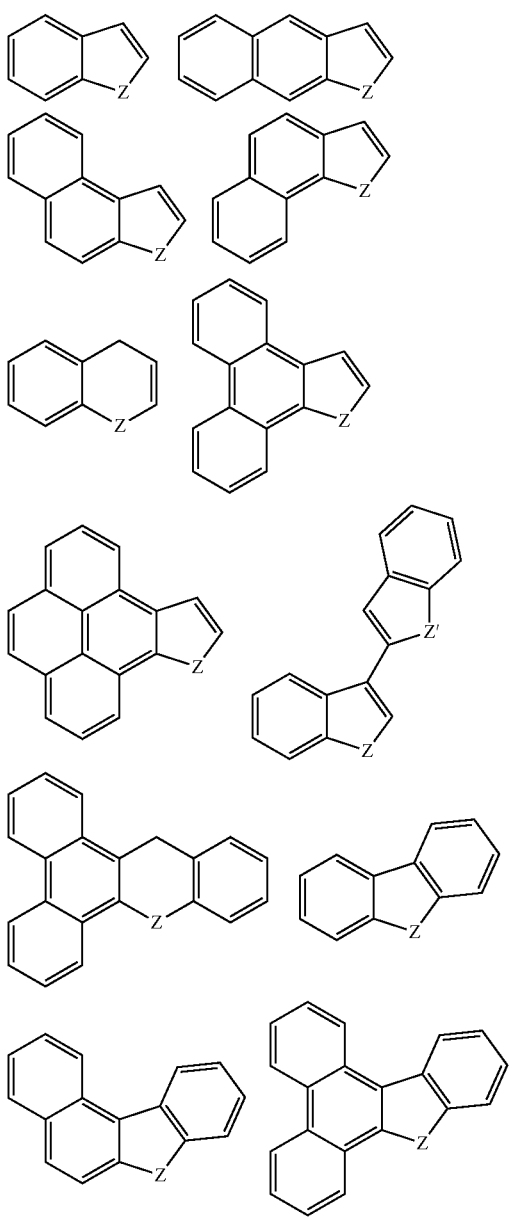
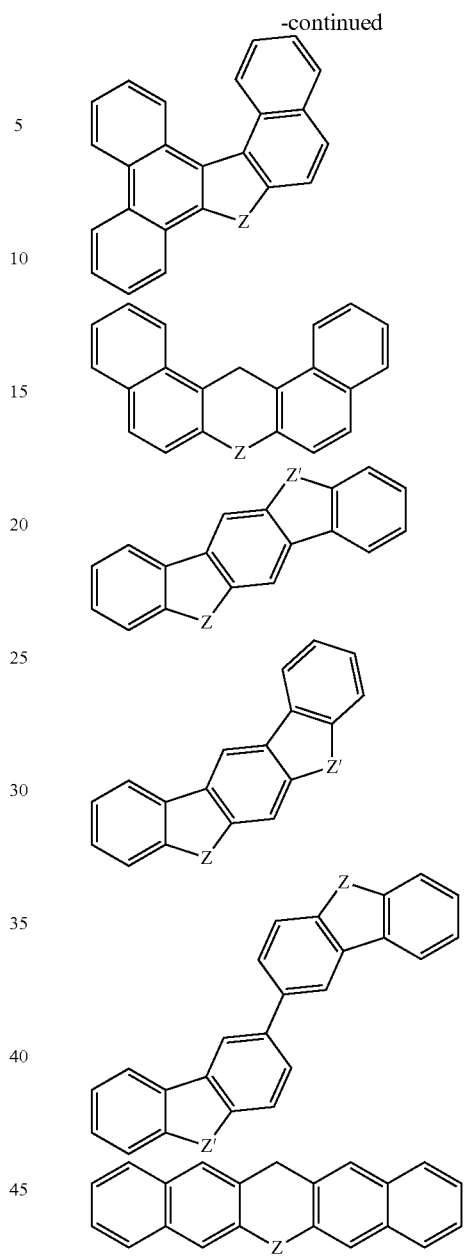
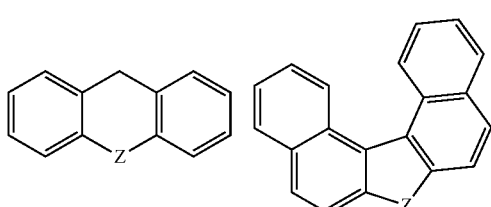
wherein, in the above compounds, Z and Z' may each independently be selected from $NR^a$, O, S, Te, and Se, in which $R^a$ is hydrogen, a substituted or unsubstituted C1 to C10 alkyl group, a halogen atom, or a combination thereof.
The monomer may be represented by one of Chemical Formulae 1-1 to 1-4:
[Chemical Formula 1-1]
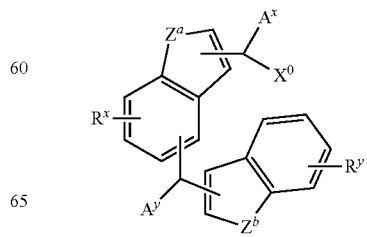

-continued

[Chemical Formula 1-2]

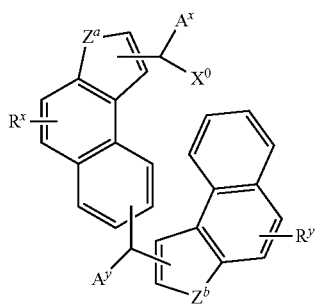

[Chemical Formula 1-3]

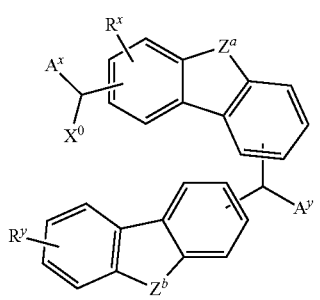

[Chemical Formula 1-4]

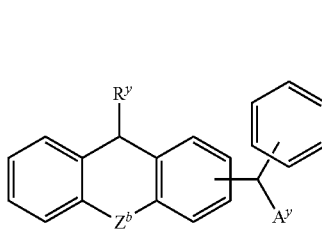

wherein, in Chemical Formulae 1-1 to 1-4, $A^x$ and $A^y$ may each independently be a substituted or unsubstituted C6 to C50 cyclic group, $Z^a$ and $Z^b$ may each independently be $NR^a$, O, S, Te, or Se, in which $R^a$ is hydrogen, a substituted or unsubstituted C1 to C10 alkyl group, a halogen atom, or a combination thereof, $R^x$ and $R^y$ may each independently be hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof, and $X^0$ may be a hydroxy group.

The monomer may have a molecular weight of about 200 to about 5,000.

The embodiments may be realized by providing an organic layer composition including a monomer represented by Chemical Formula 1, and a solvent,

[Chemical Formula 1]

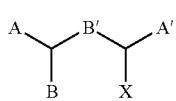

wherein, in Chemical Formula 1, A and A' are each independently a substituted or unsubstituted C6 to C50 cyclic group, B and B' are each independently a substituted or unsubstituted C2 to C50 heterocyclic group, and X is a hydroxy group.

The hetero cyclic group may include at least one of N, O, S, Te, and Se.

A and A' may each independently be a substituted or unsubstituted cyclic group of one of the following compounds:

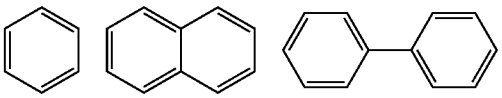

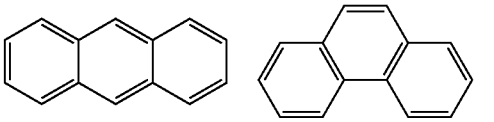

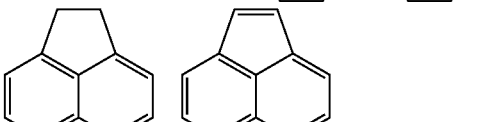

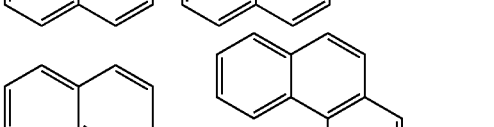

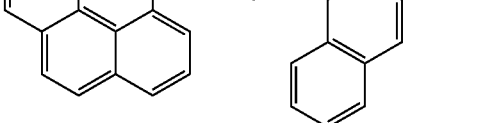

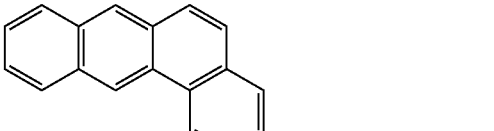

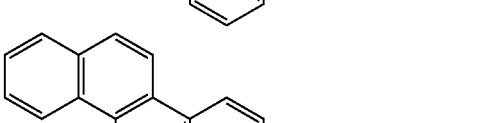

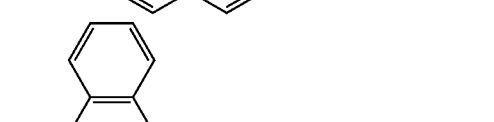

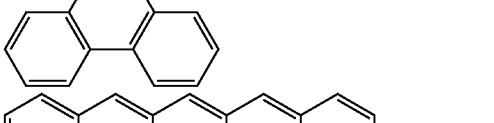

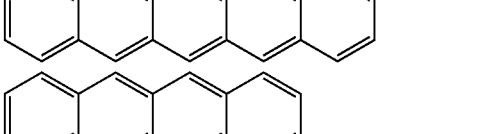

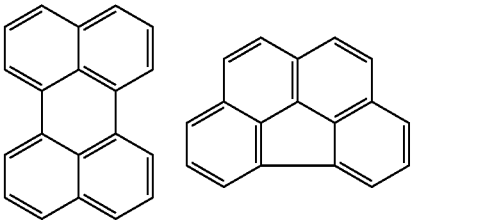

-continued
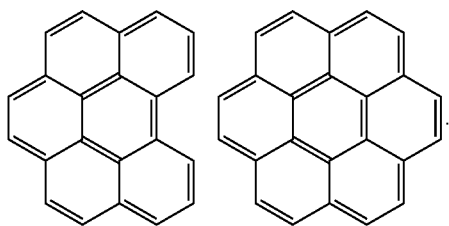
B and B' may each independently be a substituted or unsubstituted heterocyclic group of one of the following compounds:
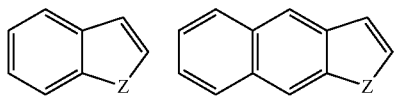
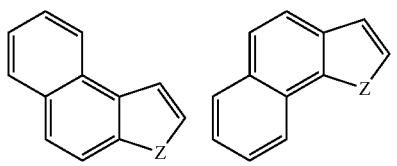
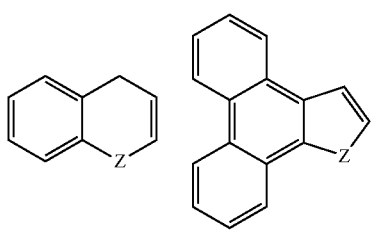
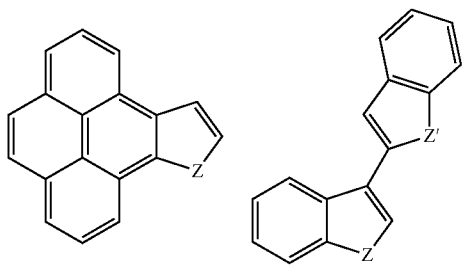
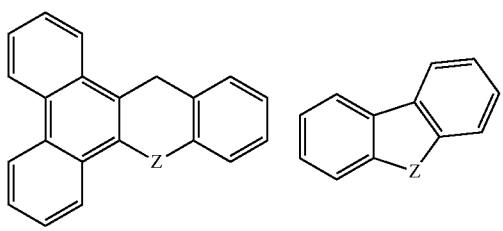
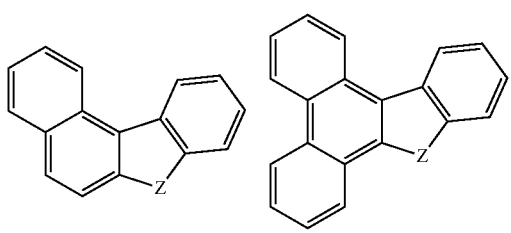
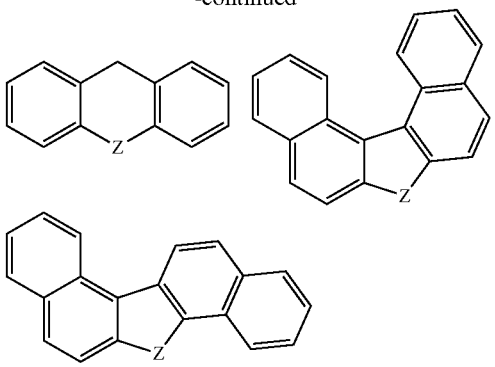
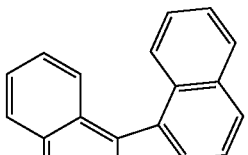
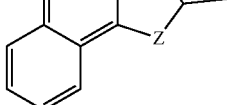
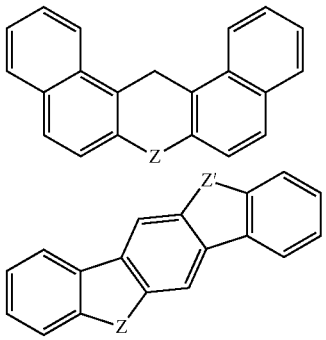
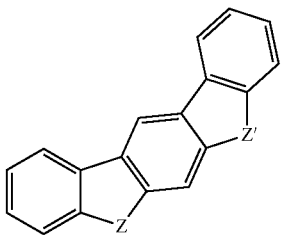
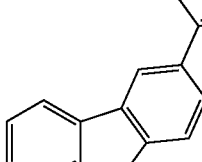
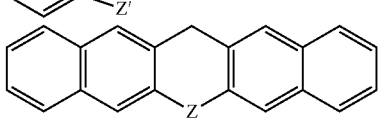
wherein, in the above compounds, Z and Z' may each independently be $NR^a$, O, S, Te, or Se, in which $R^a$ is hydrogen, a substituted or unsubstituted C1 to C10 alkyl group, a halogen atom, or a combination thereof.

The monomer may be represented by one of Chemical Formulae 1-1 to 1-4:

[Chemical Formula 1-1]

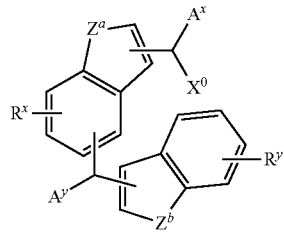

[Chemical Formula 1-2]

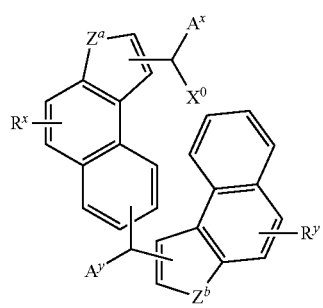

[Chemical Formula 1-3]

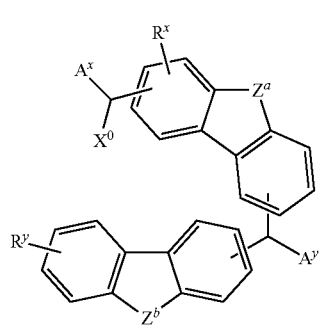

[Chemical Formula 1-4]

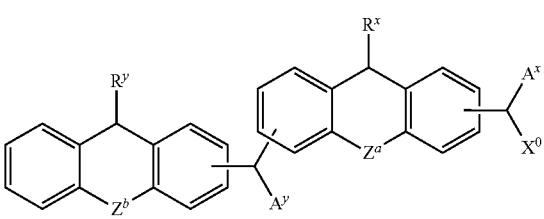

wherein, in Chemical Formulae 1-1 to 1-4, $A^x$ and $A^y$ may each independently be a substituted or unsubstituted C6 to C50 cyclic group, $Z^a$ and $Z^b$ may each independently be selected from $NR^a$, O, S, Te, and Se, in which $R^a$ is hydrogen, a substituted or unsubstituted C1 to C10 alkyl group, a halogen atom, or a combination thereof, $R^x$ and $R^y$ may each independently be hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof, and $X^0$ may be a hydroxy group.

The monomer may have a molecular weight of about 200 to about 5,000.

The monomer may be present in an amount of about 0.1 wt % to about 50 wt %, based on a total weight of the organic layer composition.

The embodiments may be realized by providing an organic layer provided by curing the organic layer composition according to an embodiment.

The organic layer may be a hardmask layer.

The embodiments may be realized by providing a method of forming a pattern, the method including providing a material layer on a substrate, applying the organic layer composition according to an embodiment on the material layer, heat-treating the organic layer composition to form a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer using the photoresist pattern to expose a part of the material layer, and etching an exposed part of the material layer.

Applying the organic layer composition includes performing a spin-on coating method.

The method may further include forming a bottom anti-reflective coating before providing the photoresist layer.

The heat-treating may be performed at about 100° C. to about 600° C.

BRIEF DESCRIPTION OF THE DRAWINGS

Features will be apparent to those of skill in the art by describing in detail exemplary embodiments with reference to the attached drawings in which:

FIG. 1 illustrates an explanation of Calculation Equation 1, for calculating out-gas amounts.

DETAILED DESCRIPTION

Figure 2:
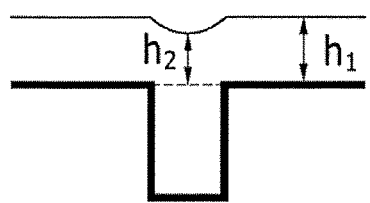
FIG. 2 illustrates an explanation of Calculation Equation 3, for evaluating planarization characteristics.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present.

As used herein, when a definition is not otherwise provided, the term 'substituted' may refer to one substituted with a substituent selected from a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C2 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C30 heterocycloalkyl group, and a combination thereof, instead of hydrogen of a compound.

As used herein, when a definition is not otherwise provided, the term 'hetero' may refer to one including 1 to 3 heteroatoms selected from N, O, S, Te, Se, and P.

Hereinafter, a compound or monomer according to one embodiment is described.

A compound or monomer according to an embodiment may be represented by Chemical Formula 1.

[Chemical Formula 1]

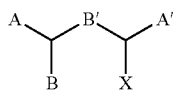

In Chemical Formula 1,

A and A' may each independently be or include, e.g., a substituted or unsubstituted C6 to C50 cyclic group.

B and B' may each independently be or include, e.g., a substituted or unsubstituted C2 to C50 heterocyclic group.

X may be, e.g., a hydroxy group.

The monomer may have a compound structure including, e.g., two substituted or unsubstituted C6 to C50 cyclic groups and two substituted or unsubstituted C2 to C50 hetero cyclic groups.

The monomer may be produced through a reaction between a nucleophile of a heterocyclic material including a heteroatom and an aldehyde-based electrophile. The monomer may induce a cyclization intramolecular or intermolecular reaction and may help improve etch resistance characteristics and pattern-forming characteristics during the formation of a thin film.

A C6 to C50 cyclic group (A') and a C2 to C50 hetero cyclic group (B') may be connected through sp3 carbon substituted with a hydroxy group (X), and the monomer may help improve gap-fill characteristics and planarization characteristics when a thin film is formed on a lower layer having a predetermined pattern in a spin-on coating method as well as further help improve solubility and thus effectively form the thin film in the spin-on coating method.

In an implementation, in Chemical Formula 1, A and A' may each independently be or include, e.g., a substituted or unsubstituted cyclic group of one of the following compounds.

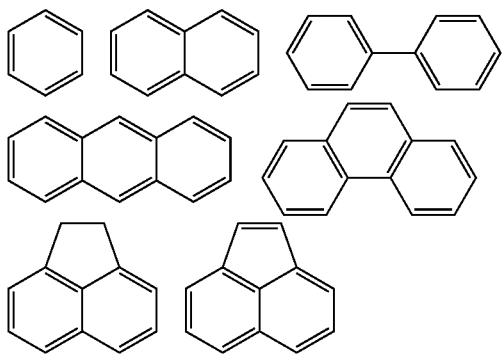

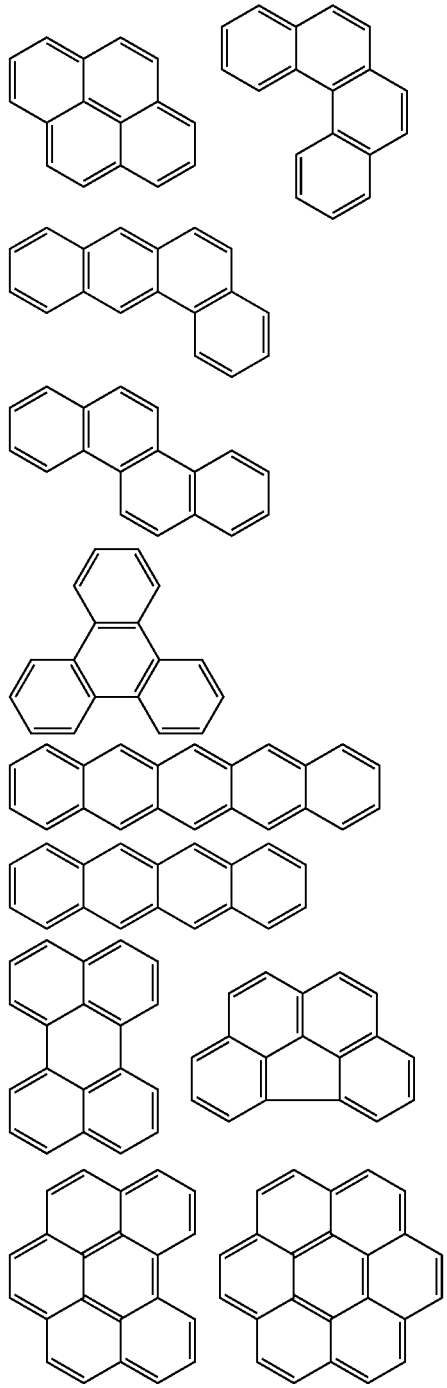

In the above compounds, linking points are not limited. In an implementation, at least one hydrogen of the above compounds may be replaced by another substituent.

In an implementation, in Chemical Formula 1, B and B' may each independently be or include, e.g., a cyclic group including at least one hetero atom selected from N, O, S, Te, and Se.

In an implementation, in Chemical Formula 1, B and B' may each independently be or include, e.g., a substituted or unsubstituted heterocyclic group of one of the following compounds.

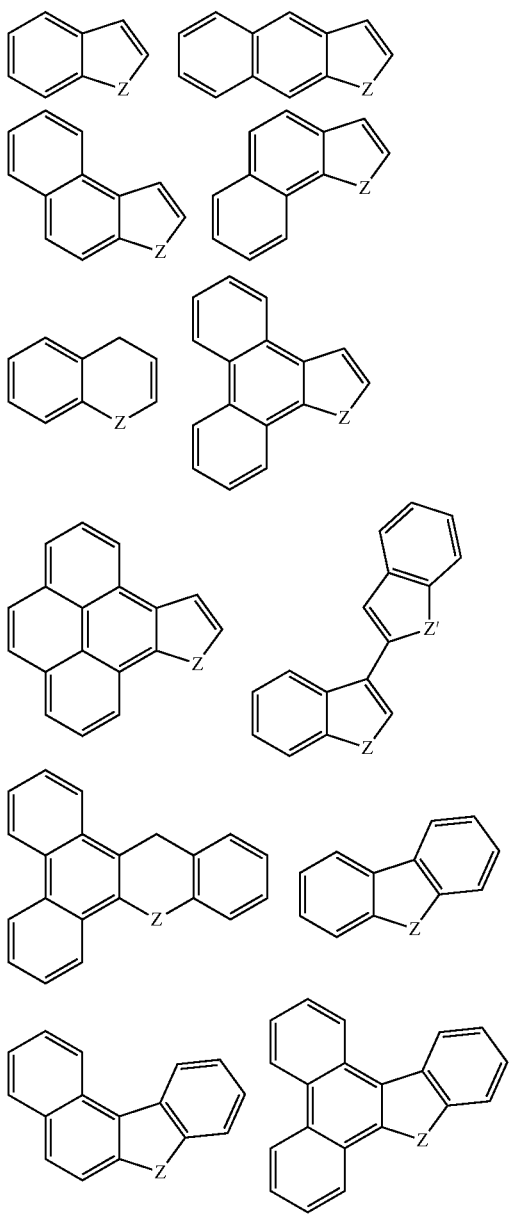
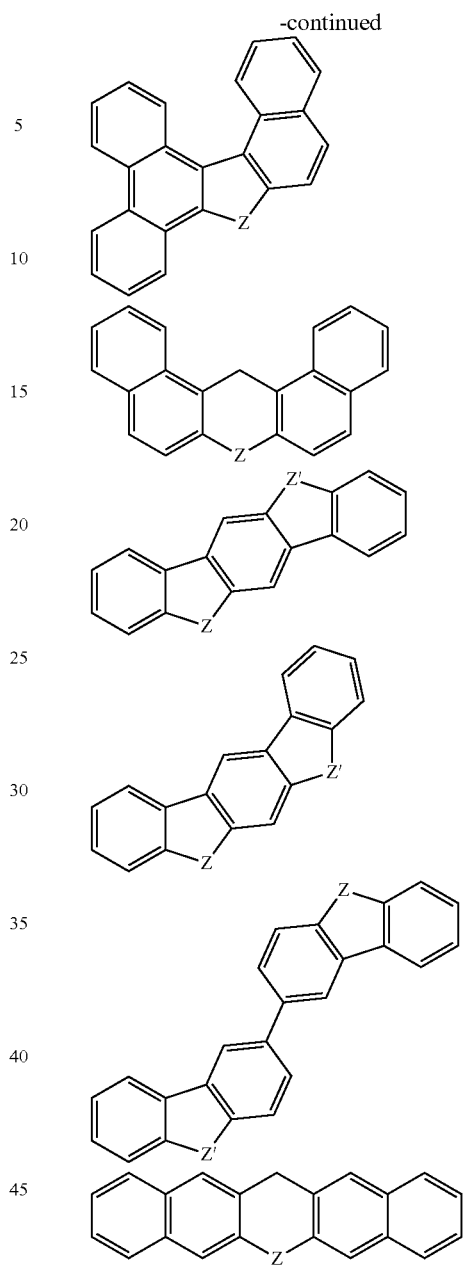
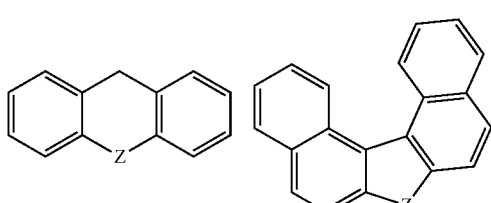
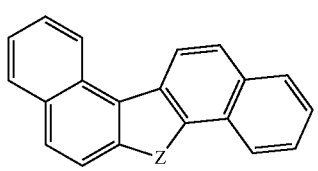

In the above compounds, Z and Z' may each independently be selected from, e.g., $NR^a$, O, S, Te, and Se (in which $R^a$ is hydrogen, a substituted or unsubstituted C1 to C10 alkyl group, a halogen atom, or a combination thereof).

In the above compounds, linking points are not limited. In an implementation, at least one hydrogen of the compounds may be replaced by another substituent.

The monomer may include high carbon-based cyclic groups and may have rigid properties and thus may help improve heat resistance, film strength, film density, and etch resistance when used as an organic layer material. In addition, the monomer may include a hetero atom inside the structure and thus may help improve a dissolution property (e.g., solubility).

In an implementation, the monomer may be represented by one of Chemical Formulae 1-1 to 1-4.

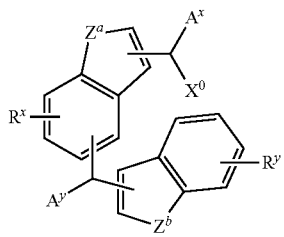

[Chemical Formula 1-1]

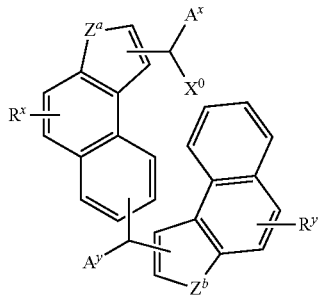

[Chemical Formula 1-2]

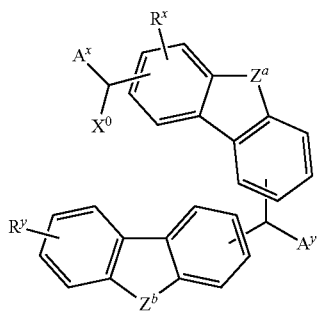

[Chemical Formula 1-3]

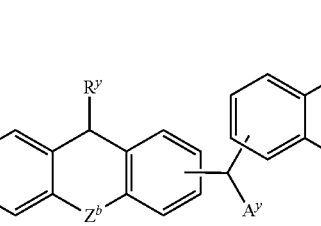

[Chemical Formula 1-4]

In Chemical Formulae 1-1 to 1-4, $A^x$ and $A^y$ may each independently be or include, e.g., a substituted or unsubstituted C6 to C50 cyclic group.

$Z^a$ and $Z^b$ may each independently be selected from, e.g., $NR^a$, O, S, Te, and Se, (in which $R^a$ is hydrogen, a substituted or unsubstituted C1 to C10 alkyl group, a halogen atom, or a combination thereof).

$R^x$ and $R^y$ may each independently be or include, e.g., hydrogen, a substituted or unsubstituted C1 to C30 alkyl group, a substituted or unsubstituted C3 to C30 cycloalkyl group, a substituted or unsubstituted C6 to C30 aryl group, a substituted or unsubstituted C7 to C30 arylalkyl group, a substituted or unsubstituted C1 to C30 heteroalkyl group, a substituted or unsubstituted C2 to C30 heterocycloalkyl group, a substituted or unsubstituted C2 to C30 heterocyclic group, a substituted or unsubstituted C2 to C30 alkenyl group, a substituted or unsubstituted C2 to C30 alkynyl group, a hydroxy group, a halogen atom, or a combination thereof.

$X^0$ may be, e.g., a hydroxy group.

The monomer may have a molecular weight of about 200 to about 5,000. When the monomer has a molecular weight within the above range, solubility of the monomer having a high carbon content for a solvent may be improved and an improved thin layer may be obtained through spin-on coating.

When the monomer is used as an organic layer material, excellent gap-fill and planarization characteristics may not only be provided when a step is present in a lower substrate (or a film) or when a pattern is formed, but a uniform thin film may also be formed without forming a pin-hole and a void during the baking or deteriorating a thickness distribution.

According to another embodiment, an organic layer composition including the monomer and a solvent may be provided.

The organic layer composition may include one or more compound or monomer represented by Chemical Formula 1.

The solvent may have sufficient dissolubility or dispersion for the monomer and may include, e.g., propylene glycol, propylene glycol diacetate, methoxy propanediol, diethylene glycol, diethylene glycol butylether, tri(ethyleneglycol)monomethylether, propylene glycol monomethylether, propylene glycol monomethylether acetate, cyclohexanone, ethyl lactate, gamma-butyrolactone, methylpyrrolidone, acetylacetone, or ethyl 3-ethoxypropionate.

The monomer may be included in an amount of about 1 to 50 wt %, based on a total weight of the organic layer composition. When the monomer is included in the range, a thickness, surface roughness, and planarization of the organic layer may be controlled.

The organic layer composition may further include a surfactant.

In an implementation, the surfactant may include, e.g., alkylbenzene sulfonate salt, alkyl pyridinium salt, polyethylene glycol, or a quaternary ammonium salt.

The surfactant may be included in an amount of about 0.001 to 3 parts by weight, based on 100 parts by weight of the organic layer composition. Within this range, the solubility may be secured while not changing the optical properties of the organic layer composition.

According to another embodiment, an organic layer manufactured using the organic layer composition may be provided. The organic layer may be, e.g., formed by coating the organic layer composition on a substrate and heat-treating it for curing and may include, e.g., a hardmask layer, a planarization layer, a sacrificial layer, a filler, and the like for an electronic device.

Hereafter, a method for forming patterns by using the organic layer composition is described.

A method of forming patterns according to one embodiment may include, e.g., providing a material layer on a substrate, applying the organic layer composition including the monomer and the solvent, heat-treating the organic layer composition including the monomer and the solvent to form a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer using the photoresist pattern to expose a part of the material layer, and etching an exposed part of the material layer.

The substrate may be, e.g., a silicon wafer, a glass substrate, or a polymer substrate.

The material layer is a material to be finally patterned, e.g., a metal layer such as an aluminum layer and a copper layer, a semiconductor layer such as a silicon layer, or an insulation layer such as a silicon oxide layer and a silicon nitride layer. The material layer may be formed through a method such as a chemical vapor deposition (CVD) process.

The organic layer composition may be the same as described above, and may be applied by spin-on coating in a form of a solution. In an implementation, a thickness of the organic layer composition may be, e.g., about 50 Å to about 10,000 Å.

The heat-treating of the organic layer composition may be performed, e.g., at about 100 to about 500° C. for about 10 seconds to about 1 hour.

The silicon-containing thin layer may be formed of, e.g., SiCN, SiOC, SiON, SiOCN, SiC, SiN, and/or the like.

In an implementation, the method may further include forming a bottom antireflective coating (BARC) before forming the photoresist layer on the silicon-containing thin layer.

Exposure of the photoresist layer may be performed using, e.g., ArF, KrF, or EUV. After exposure, heat treatment may be performed at about 100° C. to about 600° C.

In an implementation, the etching process of the exposed part of the material layer may be performed through a dry etching process using an etching gas and the etching gas may be, e.g., $CHF_3$, $CF_4$, $Cl_2$, $BCl_3$, and a mixed gas thereof.

The etched material layer may be formed in a plurality of patterns, and the plurality of patterns may include, e.g., a metal pattern, a semiconductor pattern, an insulation pattern, diverse patterns of a semiconductor integrated circuit device, or the like.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, the present disclosure is illustrated in more detail with reference to examples. However, these examples are exemplary, and the present disclosure is not limited thereto.

SYNTHESIS EXAMPLE

Synthesis Example 1

30 mmol (3.15 g) of indole, 30 mmol (3.18 g) of benzaldehyde, and 6 mmol (0.7 g) of tetramethylguanidine were put in a 100 ml round-bottomed flask. Then, 60 ml of distilled water as a solvent was added thereto, and the reaction mixture was stirred at ambient temperature for 24 hours. When the reaction was complete, the resultant was extracted with 100 ml of distilled water and 100 ml of EtOAc. After performing the extraction three times, an aqueous layer was separated from an organic layer, and the organic layer was collected. The collected organic layer was concentrated under a reduced pressure, obtaining a compound X (4.6 g, 70%). The compound X (4.6 g) was dissolved in 40 g of PGMEA, p-TsOH (10 mol %) was added thereto, and the mixture was stirred and heated at 60° C. for 2 hours. When the reaction was complete, an acid catalyst was removed by using 100 ml of distilled water and 150 ml of EtOAc. Then, an aqueous layer was separated from an organic layer, and the organic layer was collected and concentrated under a reduced pressure to remove a solvent in a predetermined amount and leave 50 ml of the organic layer. The reactants dissolved in EtOAc were dropped to 500 ml of N-hexane, forming a precipitate. The resultant was sufficiently stirred, filtered, and dried, obtaining 4 g of a compound represented by Chemical Formula 1a.

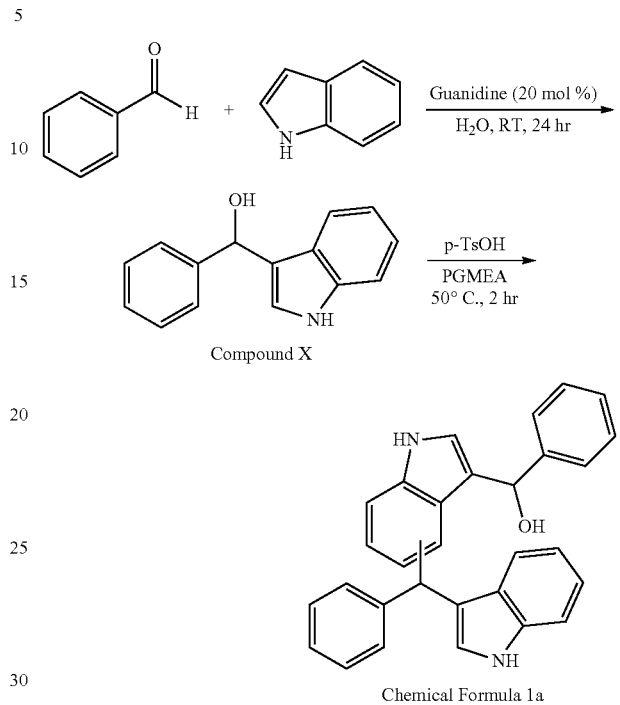

Synthesis Example 2

A compound represented by Chemical Formula 2a was obtained according to the same method as Synthesis Example 1, except for using 2-naphthaldehyde instead of the benzaldehyde.

[Chemical Formula 2a]

Synthesis Example 3

A compound represented by Chemical Formula 3a was obtained according to the same method as Synthesis Example 1, except for using 1-naphthaldehyde instead of the benzaldehyde.

[Chemical Formula 3a]

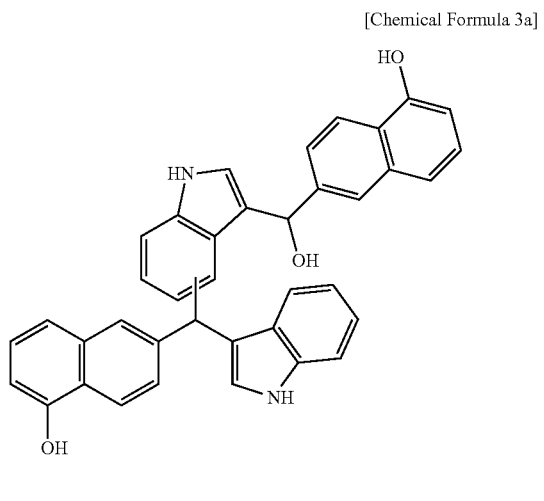

[Chemical Formula 5a]

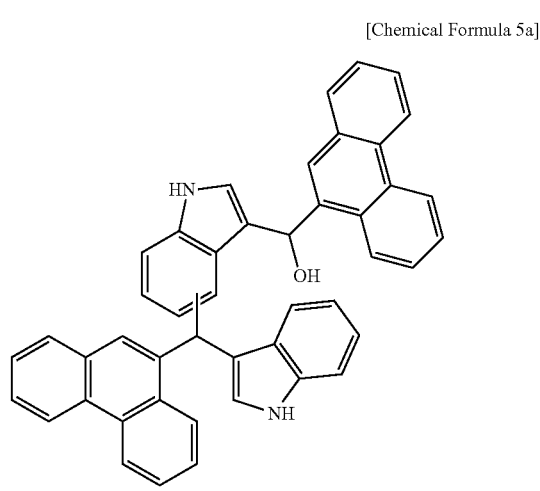

Synthesis Example 4

A compound represented by Chemical Formula 4a was obtained according to the same method as Synthesis Example 1, except for using biphenyl-4-carbaldehyde instead of the benzaldehyde.

Synthesis Example 6

A compound represented by Chemical Formula 6a was obtained according to the same method as Synthesis Example 1, except for using pyrene-1-carbaldehyde instead of the benzaldehyde.

[Chemical Formula 4a]

[Chemical Formula 6a]

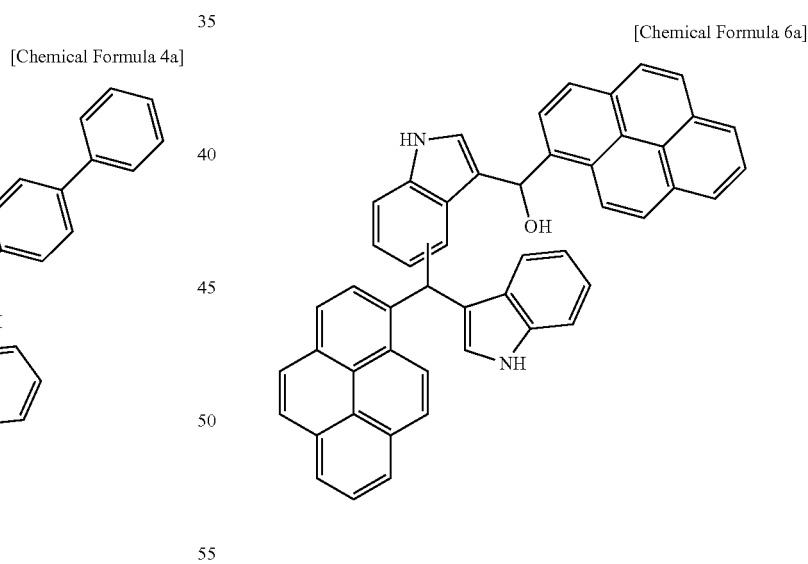

Synthesis Example 5

A compound represented by Chemical Formula 5a was obtained according to the same method as Synthesis Example 1, except for using phenanthrene-9-carbaldehyde instead of the benzaldehyde.

Synthesis Example 7

A compound represented by Chemical Formula 7a was obtained according to the same method as Synthesis Example 1, except for using hydroxy-pyrene-1-carbaldehyde instead of the benzaldehyde.

[Chemical Formula 7a]

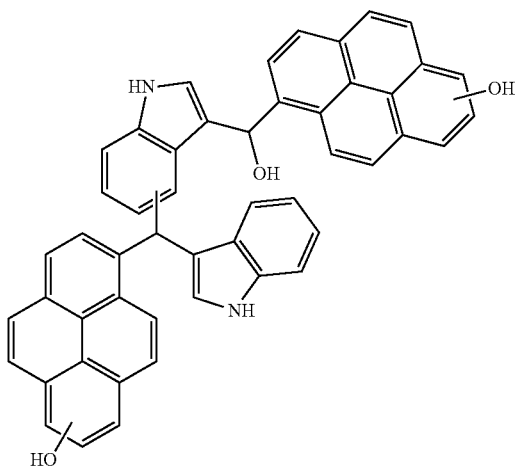

Synthesis Example 8

A compound represented by Chemical Formula 8a was obtained according to the same method as Synthesis Example 1, except for using coronene-1-carbaldehyde instead of the benzaldehyde.

[Chemical Formula 8a]

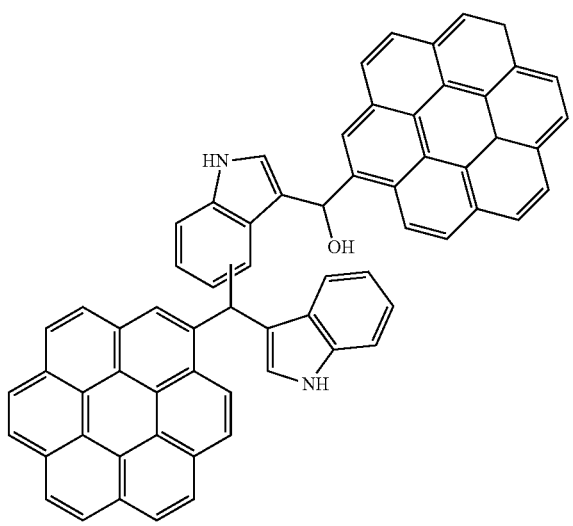

Synthesis Example 9

A compound represented by Chemical Formula 9a was obtained according to the same method as Synthesis Example 1, except for using 4-hydroxyindole instead of the indole.

[Chemical Formula 9a]

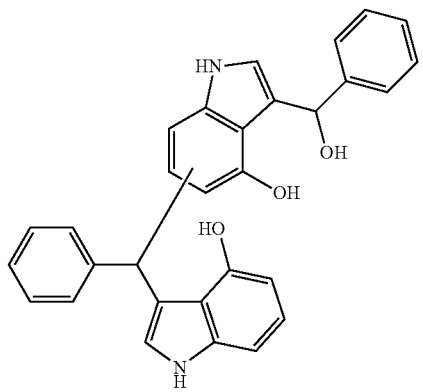

Synthesis Example 10

A compound represented by Chemical Formula 10a was obtained according to the same method as Synthesis Example 1, except for using 4-hydroxyindole instead of the indole and pyrene-1-carbaldehyde instead of the benzaldehyde.

[Chemical Formula 10a]

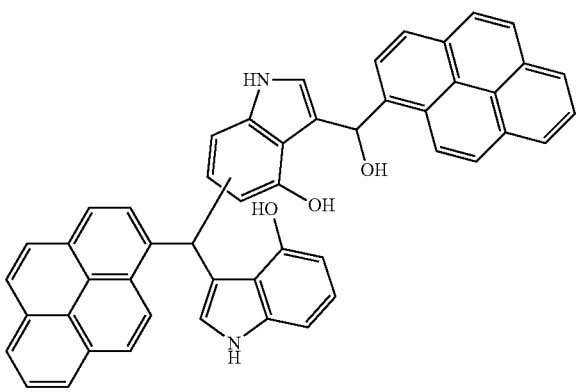

Synthesis Example 11

A compound represented by Chemical Formula 11a was obtained according to the same method as Synthesis Example 1, except for using 4-hydroxyindole instead of the indole and hydroxy-pyrene-1-carbaldehyde instead of the benzaldehyde.

[Chemical Formula 11a]

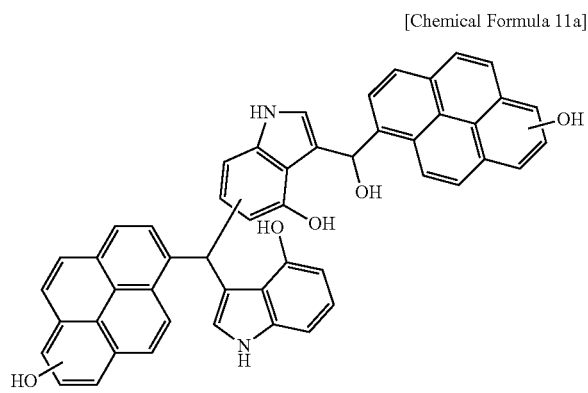

Synthesis Example 12

A compound represented by Chemical Formula 12a was obtained according to the same method as Synthesis Example 1, except for using 3H-benzo[e]indole instead of the indole.

[Chemical Formula 12a]

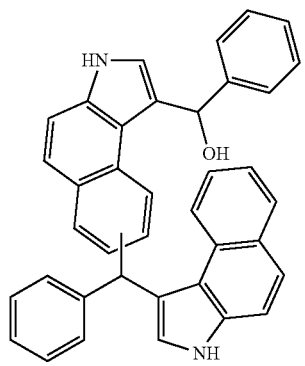

Synthesis Example 13

A compound represented by Chemical Formula 13a was obtained according to the same method as Synthesis Example 1, except for using 3H-benzo[e]indole instead of the indole and pyrene-1-carbaldehyde instead of the benzaldehyde.

[Chemical Formula 13a]

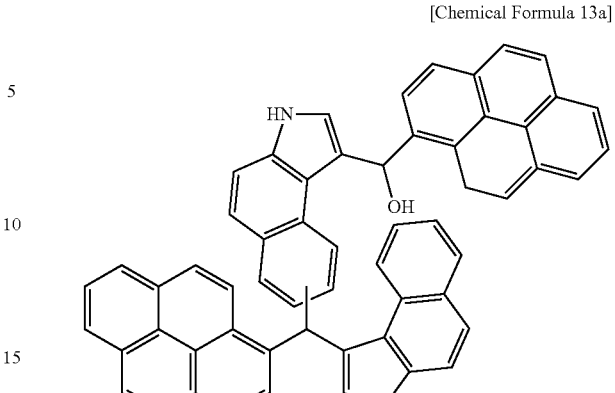

Synthesis Example 14

A compound represented by Chemical Formula 14a was obtained according to the same method as Synthesis Example 1, except for using 3H-benzo[e]indole instead of the indole and hydroxy-pyrene-1-carbaldehyde instead of the benzaldehyde.

[Chemical Formula 14a]

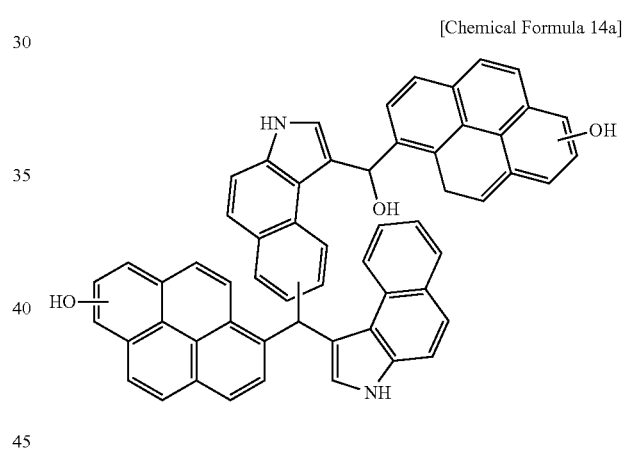

Synthesis Example 15

100 mmol (16.7 g) of carbazole and 100 mmol (14 g) of benzoylchloride were put in a 250 ml round-bottomed flask. Then, 150 ml of DCE was added thereto, and the temperature of the flask was cooled down to 0° C. Subsequently, 120 mmol (15.96 g) of $AlCl_3$ was divided and slowly added thereto, and then, the mixture was heated up to ambient temperature. When the reaction was complete by checking it with TLC, the reaction mixture was added to 1500 ml of a MeOH solution, forming a precipitate. The precipitate was filtered and dried in an oven, obtaining 90% of a compound A. Then, 93 mmol (25 g) of the compound A was dissolved in 200 ml of THF/DIW=1/1, and the reactants were cooled down to 0° C. Subsequently, 150 mmol (5.7 g) of $NaBH_4$ was slowly added to the reactants to perform a reaction.

When the reaction was complete, the resultant was worked up with 300 ml of ethyl acetate and 300 ml of an $NH_4Cl$ solution, separating an organic layer. Then, a solvent therein was removed by using a decompression drier and left in an amount of 50 ml. Subsequently, 50 ml of the obtained solution was added to 1000 ml of n-Hx in a dropwise fashion, obtaining a precipitate. The obtained precipitate was filtered, obtaining 85% of a compound B. 76 mmol (21 g) of the compound B was dissolved in 100 g of PGMEA, and 8 mmol (1.5 g) of p-toluene sulfonic acid monohydrate was added thereto. Subsequently, the mixture was heated up to 50° C. and stirred.

When the compound exhibited as a main structure on a GPC, 300 ml of distilled water and 300 ml of EtOAc were used to remove an acid catalyst. Then, an aqueous layer was separated from an organic layer, and the organic layer was collected and concentrated under a reduced pressure to remove a solvent in a predetermined amount and left in an amount of about 50 ml. The reactants dissolved in EtOAc were dropped into 1,000 ml of N-hexane, forming a precipitate. The mixture was sufficiently stirred, filtered, and dried, obtaining 16 g of a compound represented by Chemical Formula 15a.

[Chemical Formula 15a]

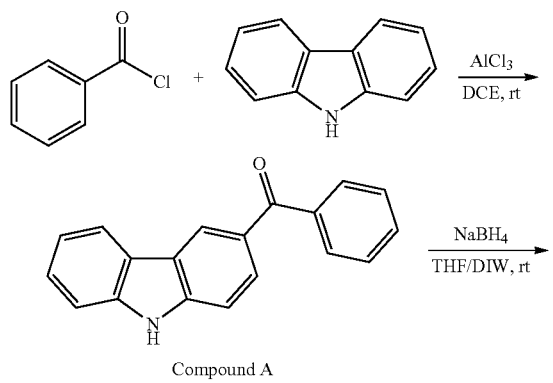

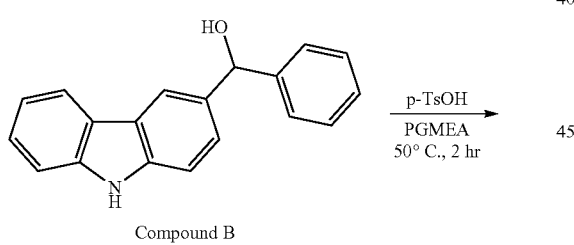

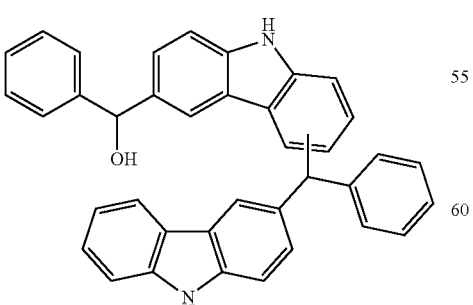

Chemical Formula 15a

Synthesis Example 16

A compound represented by Chemical Formula 16a was obtained according to the same method as Synthesis Example 15, except for using 6-hydroxyl-2-naphtholyl chloride instead of the benzolylchloride.

[Chemical Formula 16a]

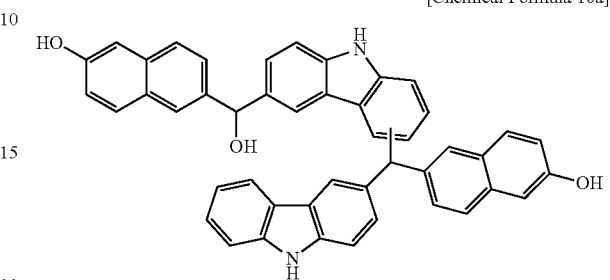

Synthesis Example 17

A compound represented by Chemical Formula 17a was obtained according to the same method as Synthesis Example 15, except for using hydroxy-pyrene-1-carbaldehyde instead of the benzolylchloride.

[Chemical Formula 17a]

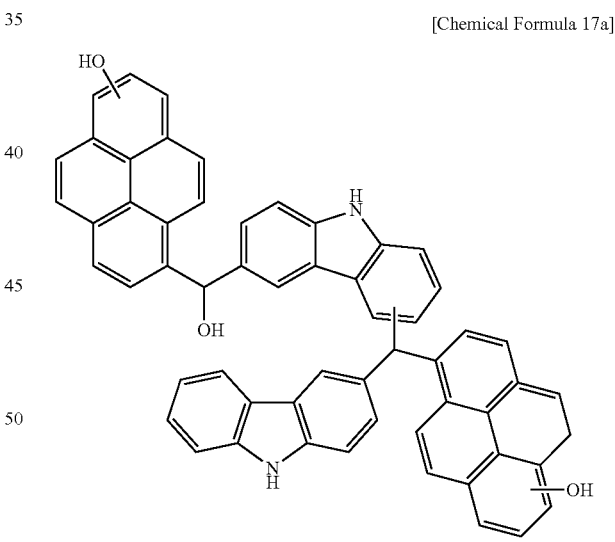

Synthesis Example 18

A compound represented by Chemical Formula 18a was obtained according to the same method as Synthesis Example 15, except for using 9-phenyl-9H-xanthene instead of the carbazole.

[Chemical Formula 18a]

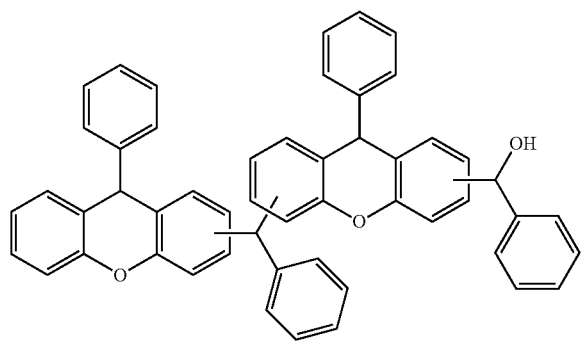

Synthesis Example 19

A compound represented by Chemical Formula 19a was obtained according to the same method as Synthesis Example 15, except for using benzothiophene instead of the carbazole.

[Chemical Formula 19a]

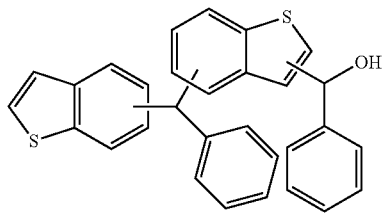

Comparative Synthesis Example 1

21 g (0.057 mol) of 9,9-bis(4-hydroxyphenyl)-9H-fluorene and 9.6 g (0.057 mol) of 4,4-methoxymethylbenzene were sequentially put in a 500 ml flask and dissolved in 51 g of propylene glycol monomethylether acetate (PGMEA), 0.001 mol of p-toluenesulfonic acid monohydrate was added thereto, and the mixture was stirred at 100° C. for 5 hours. When a specimen taken from the polymerization reactants every hour had a weight average molecular weight in a range of 3,500 to 4,000, the reaction was completed, obtaining a compound including a moiety represented by Chemical Formula 3.

[Chemical Formula 3]

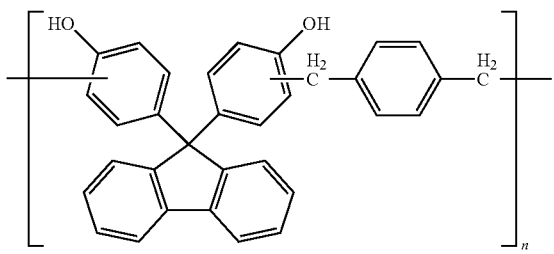

Comparative Synthesis Example 2

35 g (0.1 mol) of 9,9-bis(4-hydroxyphenyl)-9H-fluorene, 14.4 g, (0.1 mol) of 1-naphthol, and 1.2 g (0.034 mol) of paraformaldehyde were put in a 500 ml flask. Subsequently, 0.19 g (0.34 mol) of p-toluenesulfonic acid monohydrate was dissolved in 162 g of propylene glycol monomethyl ether acetate (PGMEA), and the solution was put in a reactor. The mixture was stirred at 100° C. for 5 hours. When a specimen taken from the polymerization reactants every hour had a weight average molecular weight ranging from 3,500 to 4,000, the reaction was completed, obtaining a compound including a moiety represented by Chemical Formula 4.

[Chemical Formula 4]

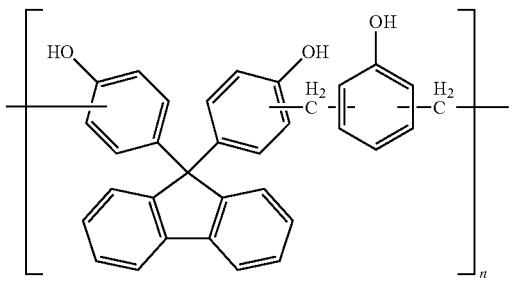

Preparation of Hardmask Composition

Example 1

The compound according to Synthesis Example 1 was dissolved in a mixed solvent of propylene glycolmonomethyl ether acetate (PGMEA) and ethyl lactate (EL) (7:3 (v/v)), and the solution was filtered with a 0.1 μm TEFLON (tetrafluoroethylene) filter, preparing a hardmask composition. The compound was adjusted to have a weight in a range of 5.0 wt % to 15.0 wt % based on the total weight of the hardmask composition (depending on a desired thickness).

Examples 2 to 19

Each hardmask composition according to Examples 2 to 10 was prepared according to the same method as Example 1 except for respectively using the compounds of Synthesis Example 2 to 19 instead of the compound of Synthesis Example 1.

Comparative Examples 1 and 2

A hardmask composition was prepared according to the same method as Example 1 except for respectively using the compounds of Comparative Synthesis Examples 1 and 2 instead of the compound of Synthesis Example 1.

Evaluation 1: Film Density

Each hardmask composition according to Examples 1 to 19 and Comparative Examples 1 and 2 was spin-on coated on a silicon wafer and baked on a hot plate at 400° C. for 2 minutes, forming an about 1,000 Å-thick thin film. The thin film was measured regarding film density by using an X-ray diffraction equipment made by PANalytical.

The results are provided in Table 1.

TABLE 1

|  | Film density (g/cm³) |
| --- | --- |
| Example 1 | 1.37 |
| Example 2 | 1.38 |
| Example 3 | 1.39 |
| Example 4 | 1.36 |
| Example 5 | 1.34 |
| Example 6 | 1.39 |
| Example 7 | 1.41 |
| Example 8 | 1.39 |
| Example 9 | 1.40 |
| Example 10 | 1.41 |
| Example 11 | 1.44 |
| Example 12 | 1.37 |
| Example 13 | 1.39 |
| Example 14 | 1.40 |
| Example 15 | 1.36 |
| Example 16 | 1.39 |
| Example 17 | 1.40 |
| Example 18 | 1.29 |
| Example 19 | 1.30 |
| Comparative Example 1 | 1.21 |
| Comparative Example 2 | 1.23 |

Referring to Table 1, each thin film respectively formed of the hardmask compositions according to Examples 1 to 19 exhibited a higher film density than each thin film respectively formed of the hardmask compositions according to Comparative Examples 1 and 2.

For example, the hardmask compositions according to Examples 1 to 19 all formed dense and firm thin films, compared with the hardmask compositions according to Comparative Examples 1 and 2.

Evaluation 2: Out-Gas

The hardmask compositions according to Examples 1 to 19 and Comparative Examples 1 and 2 were respectively coated to be about 2,000 Å thick on a silicon wafer and baked at 400° C. for 5 minutes, and out-gas generated during the baking was measured by using QCM (Quartz Crystal Microbalance), and the amount (ng) of the out-gas was calculated according to Calculation Equation 1 in FIG. 1.

The results are provided in Table 2.

TABLE 2

|  | Out-gas amount (ng) |
| --- | --- |
| Example 1 | 82 |
| Example 2 | 78 |
| Example 3 | 75 |
| Example 4 | 70 |
| Example 5 | 72 |
| Example 6 | 68 |
| Example 7 | 57 |
| Example 8 | 65 |
| Example 9 | 80 |
| Example 10 | 59 |
| Example 11 | 49 |
| Example 12 | 76 |
| Example 13 | 59 |
| Example 14 | 56 |
| Example 15 | 59 |
| Example 16 | 58 |
| Example 17 | 57 |
| Example 18 | 60 |
| Example 19 | 64 |
| Comparative Example 1 | 101 |
| Comparative Example 2 | 98 |

Referring to Table 2, each thin film respectively formed of the hardmask compositions according to Examples 1 to 19 generated a relatively small amount of out-gas during the baking at a high temperature of 400° C., compared with each thin film respectively formed of the hardmask compositions according to Comparative Examples 1 and 2. Accordingly, the hardmask compositions according to Examples 1 to 19 may be advantageously applied to a high temperature process.

Evaluation 3: Etch Resistance

The hardmask compositions according to Examples 1 to 19 and Comparative Examples 1 and 2 were respectively spin-on coated on a silicon wafer and baked on a hot plate at 400° C. for 2 minutes, forming an about 4,000 Å-thick thin film. The thickness of the thin film was measured by using a thin film thickness-measurer made by K-MAC.

Subsequently, the thin film was dry-etched respectively with $N_2/O_2$ mixed gas and CFx mixed gas for 60 seconds and for 100 seconds, and then, the thickness of the thin film was measured.

The etch resistance of the thin film was evaluated from a bulk etch rate (BER) as shown in Calculation Equation 2.

[Calculation Equation 2]

Bulk etch rate (BER)=(Initial thickness of thin film−Thickness of thin film after etching)/Etching time (Å/s)

The results are provided in Table 3.

TABLE 3

|  | Bulk etch rate (Å/sec) | |
| --- | --- | --- |
|  | $N_2O_2$ etch | $CF_x$ etch |
| Example 1 | 28.4 | 24.7 |
| Example 2 | 27.9 | 23.5 |
| Example 3 | 28.3 | 24.6 |
| Example 4 | 27.5 | 25.6 |
| Example 5 | 26.3 | 26.7 |
| Example 6 | 24.2 | 21.0 |
| Example 7 | 26.0 | 20.7 |
| Example 8 | 24.9 | 22.9 |
| Example 9 | 26.3 | 21.2 |
| Example 10 | 25.5 | 21.0 |
| Example 11 | 26.7 | 19.5 |
| Example 12 | 25.6 | 25.0 |
| Example 13 | 23.2 | 21.9 |
| Example 14 | 24.0 | 21.6 |
| Example 15 | 27.5 | 24.5 |
| Example 16 | 27.1 | 24.0 |
| Example 17 | 25.6 | 23.9 |
| Example 18 | 27.5 | 25.9 |
| Example 19 | 28.1 | 27.0 |
| Comparative Example 1 | 33.0 | 29.9 |
| Comparative Example 2 | 31.9 | 28.7 |

Referring to Table 3, each thin film respectively formed of the hardmask compositions according to Examples 1 to 19 exhibited a lower bulk etch rate than each thin film respectively formed of the hardmask compositions according to Comparative Examples 1 and 2.

Accordingly, the hardmask compositions according to Examples 1 to 19 showed high etch resistance, compared with the hardmask compositions according to Comparative Examples 1 and 2.

Evaluation 4: Gap-Fill and Planarization Characteristics

The hardmask compositions according to Examples 1 to 19 and Comparative Examples 1 and 2 were respectively spin-on coated on a patterned silicon wafer and baked at 400° C. for 2 minutes, and then, gap-fill characteristics and planarization characteristics were examined by using FE-SEM equipment.

The gap-fill characteristics were evaluated by examining the cross-section of the pattern with an electron scanning microscope (SEM) to see whether there was a void, and the planarization characteristics were evaluated by measuring the thickness of the hardmask layer from the SEM image of the pattern cross-section and putting it in Calculation Equation 3 in FIG. 2. For example, the planarization characteristics were considered excellent when a difference between h1 and h2 was small.

The h1 was 2,000 Å after the baking by adjusting the amount of a compound included in the hardmask compositions according to Examples 1 to 19 and Comparative Examples 1 and 2.

The results are provided in Table 4.

TABLE 4

| | Planarization characteristics (h1-h2, Å) | | Gap-fill characteristics (void: yes/no) |
|---|---|---|---|
| | aspect ratio (1:2) | aspect ratio (1:10) | |
| Example 1 | 87 | 198 | No void |
| Example 2 | 79 | 175 | No void |
| Example 3 | 78 | 169 | No void |
| Example 4 | 88 | 186 | No void |
| Example 5 | 90 | 180 | No void |
| Example 6 | 95 | 160 | No void |
| Example 7 | 85 | 149 | No void |
| Example 8 | 97 | 174 | No void |
| Example 9 | 72 | 175 | No void |
| Example 10 | 82 | 156 | No void |
| Example 11 | 69 | 139 | No void |
| Example 12 | 76 | 176 | No void |
| Example 13 | 86 | 180 | No void |
| Example 14 | 80 | 177 | No void |
| Example 15 | 87 | 193 | No void |
| Example 16 | 80 | 170 | No void |
| Example 17 | 80 | 155 | No void |
| Example 18 | 85 | 173 | No void |
| Example 19 | 91 | 178 | No void |
| Comparative Example 1 | 106 | 253 | Void |
| Comparative Example 2 | 109 | 280 | Void |

Referring to Table 4, the hardmask compositions according to Examples 1 to 19 showed excellent planarization, compared with the hardmask compositions according to Comparative Examples 1 and 2 and also, no void under a condition of a deep pattern depth (an aspect ratio=1:15) and thus exhibited excellent gap-fill characteristics.

By way of summation and review, a hardmask layer may play a role of an interlayer transferring the fine pattern of the photoresist to a material layer through a selective etching process. Accordingly, the hardmask layer may have characteristics such as heat resistance, etch resistance, and the like to endure multi-etching processes.

A spin-on coating method (instead of a chemical vapor deposition (CVD) method) has been considered to form the hardmask layer. For example, heat resistance and etch resistance may have a trade-off relationship with spin-on characteristics, and an organic layer material may usefully satisfy all the characteristics.

The embodiments may provide a monomer that is applicable to a spin-on coating method due to improved solubility characteristics as well as excellent mechanical characteristics, etch resistance, and heat resistance.

The embodiments may provide an organic layer having excellent etch resistance, heat resistance, and planarization characteristics.

The embodiments may provide a monomer having good solubility characteristics as well as excellent etch resistance and heat resistance. The embodiments may provide an organic layer manufactured using the monomer and that has excellent mechanical characteristics and film surface flatness.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic layer composition, comprising:
    a monomer represented by one of Chemical Formulae 1-1, 1-2, and 1-4; and
    a solvent,

[Chemical Formula 1-1]

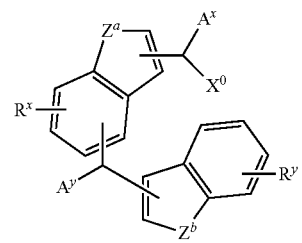

wherein, in Chemical Formula 1-1,
$A^x$ and $A^y$ are each independently a substituted or unsubstituted cyclic group of one of the following compounds:

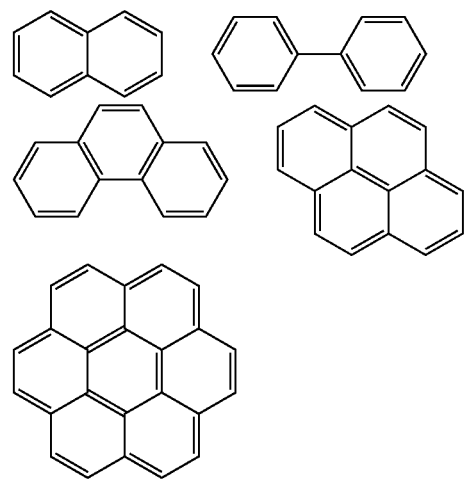

$Z^a$ and $Z^b$ are each independently $NR^a$, in which $R^a$ is hydrogen, a substituted or unsubstituted C1 to C10 alkyl group, or a combination thereof, $R^x$ and $R^y$ are each independently hydrogen, a substituted or unsubstituted C1 to C30 alkyl group, a substituted or unsubstituted C6 to C30 aryl group, or a combination thereof, and $X^0$ is a hydroxy group,

[Chemical Formula 1-2]

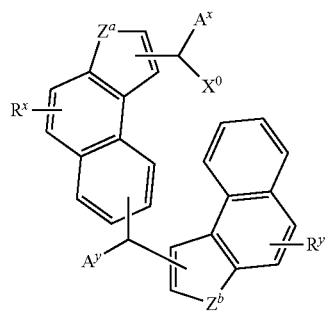

[Chemical Formula 1-4]

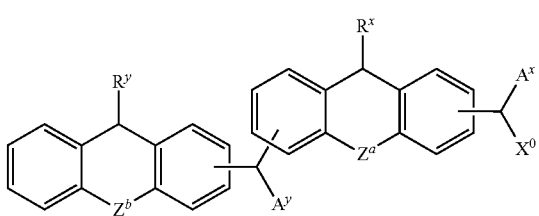

wherein, in Chemical Formulae 1-2 and 1-4,
$A^x$ and $A^y$ are each independently a substituted or unsubstituted cyclic group of one of the following compounds:

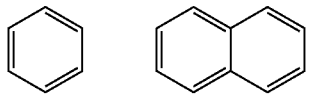

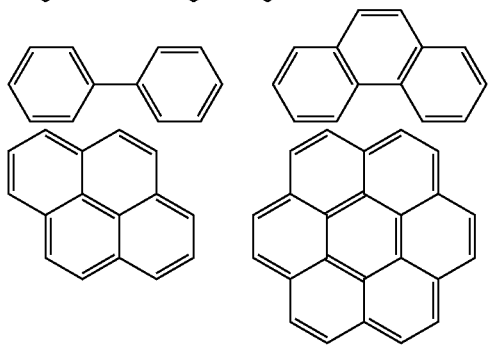

$Z^a$ and $Z^b$ are each independently $NR^a$, O, or S, in which $R^a$ is hydrogen, a substituted or unsubstituted C1 to C10 alkyl group, or a combination thereof,
$R^x$ and $R^y$ are each independently hydrogen, a substituted or unsubstituted C6 to C30 aryl group, a hydroxy group, a halogen atom, or a combination thereof, and
$X^0$ is a hydroxy group.

2. The organic layer composition as claimed in claim 1, wherein the monomer has a molecular weight of about 200 to about 5,000.

3. The organic layer composition as claimed in claim 1, wherein the monomer is present in an amount of about 0.1 wt % to about 50 wt %, based on a total weight of the organic layer composition.

4. An organic layer provided by curing the organic layer composition as claimed in claim 1.

5. The organic layer as claimed in claim 4, wherein the organic layer is a hardmask layer.

6. A method of forming a pattern, the method comprising:
providing a material layer on a substrate,
applying the organic layer composition as claimed in claim 1 on the material layer,
heat-treating the organic layer composition to form a hardmask layer,
forming a silicon-containing thin layer on the hardmask layer,
forming a photoresist layer on the silicon-containing thin layer,
exposing and developing the photoresist layer to form a photoresist pattern,
selectively removing the silicon-containing thin layer and the hardmask layer using the photoresist pattern to expose a part of the material layer, and
etching an exposed part of the material layer.

7. The method as claimed in claim 6, wherein applying the organic layer composition includes performing a spin-on coating method.

8. The method as claimed in claim 6, further comprising forming a bottom antireflective coating before providing the photoresist layer.

9. The method as claimed in claim 6, wherein the heat-treating is performed at about 100° C. to about 600° C.

10. An organic layer composition, comprising:
a monomer; and
a solvent,
wherein the monomer is one of the following compounds:

Chemical Formula 2a

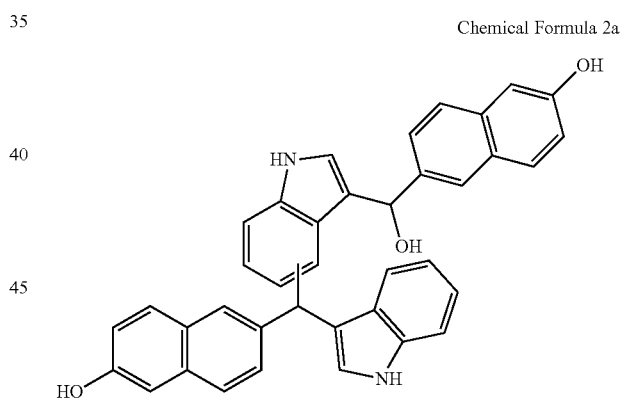

Chemical Formula 3a

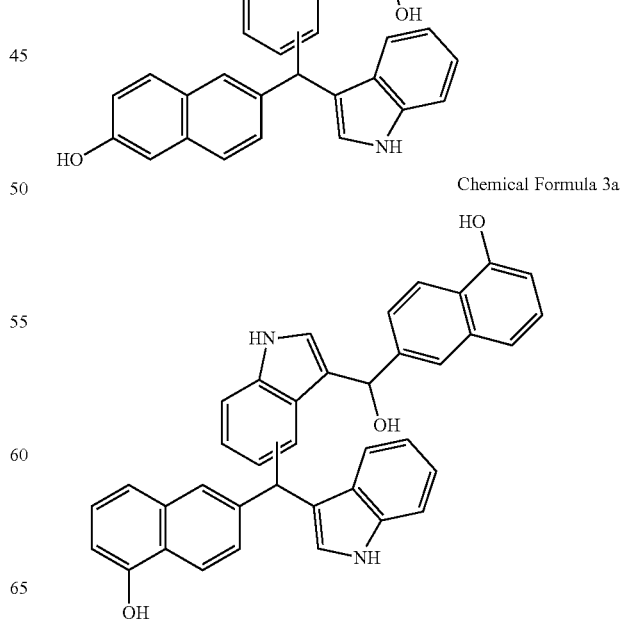

Chemical Formula 4a
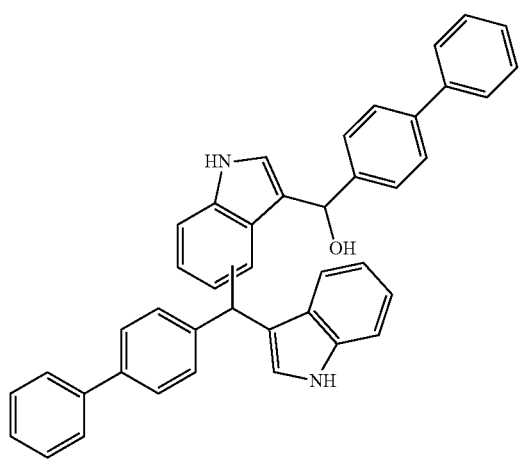
Chemical Formula 5a
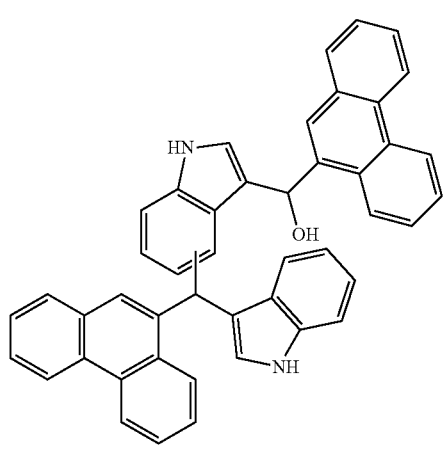
Chemical Formula 6a
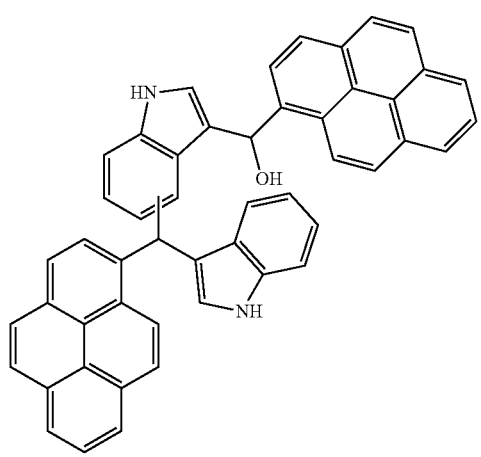
Chemical Formula 7a
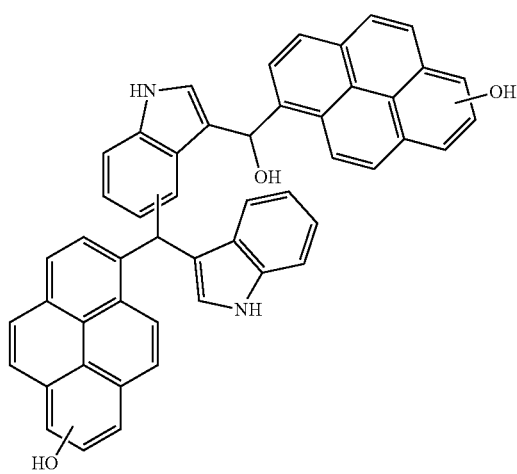
Chemical Formula 8a
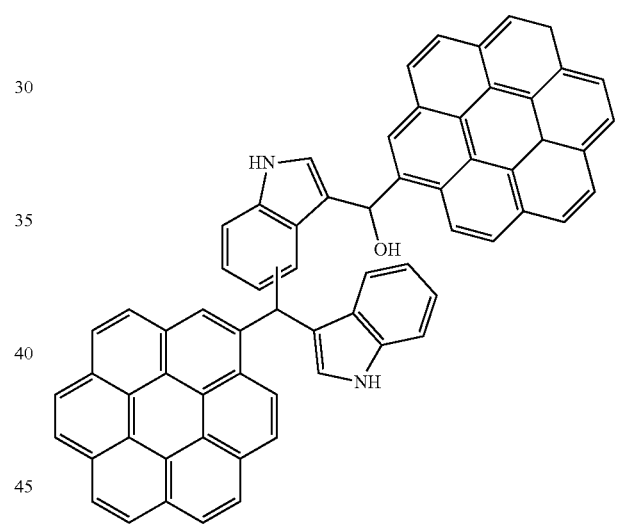
Chemical Formula 9a
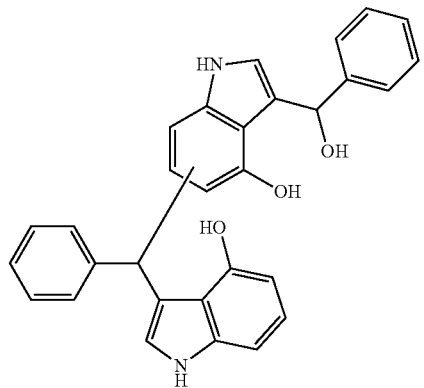

Chemical Formula 10a
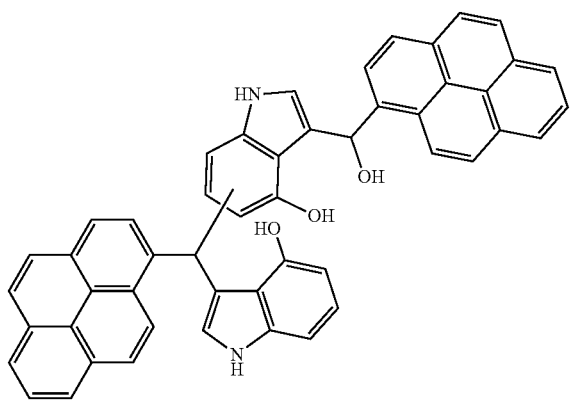
Chemical Formula 11a
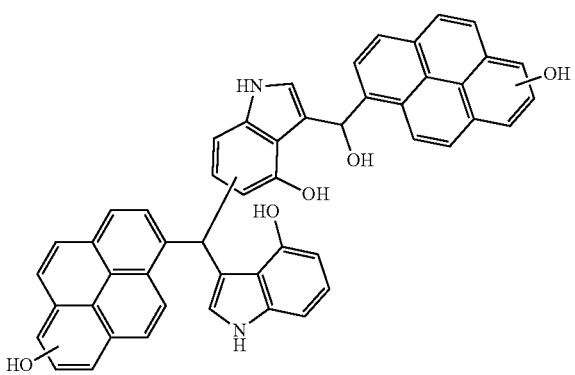
Chemical Formula 12a
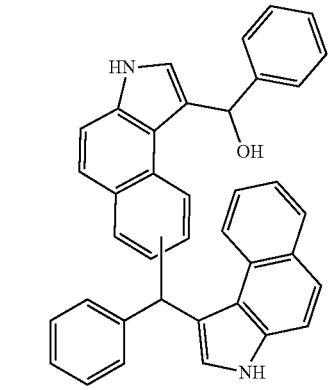
Chemical Formula 13a
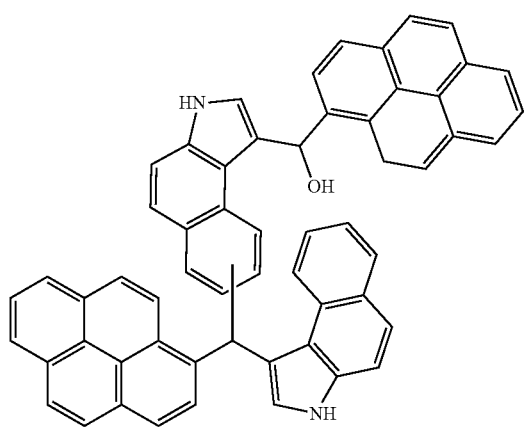
Chemical Formula 14a
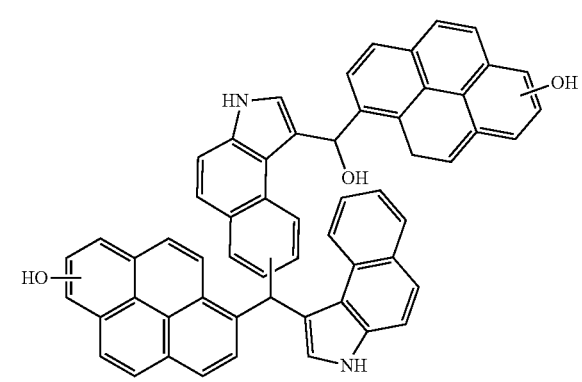
Chemical Formula 15a
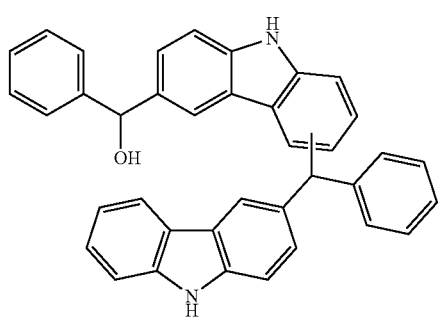
Chemical Formula 16a
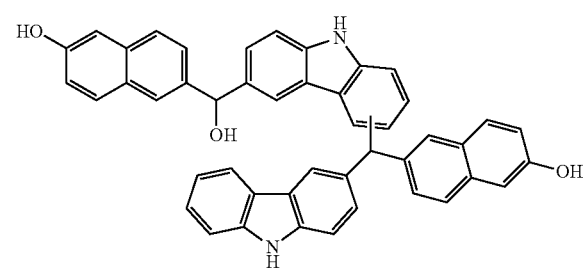
Chemical Formula 17a
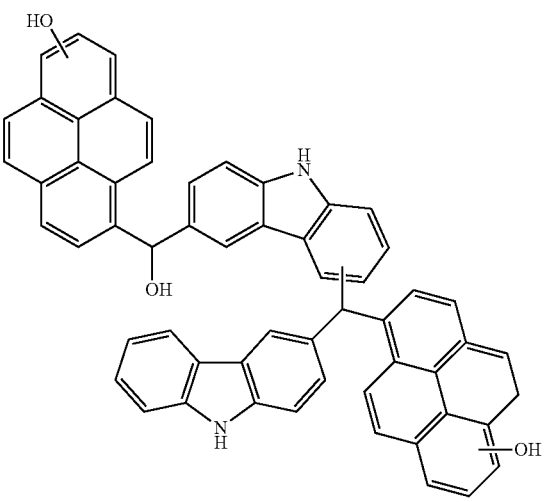

-continued
Chemical Formula 18a
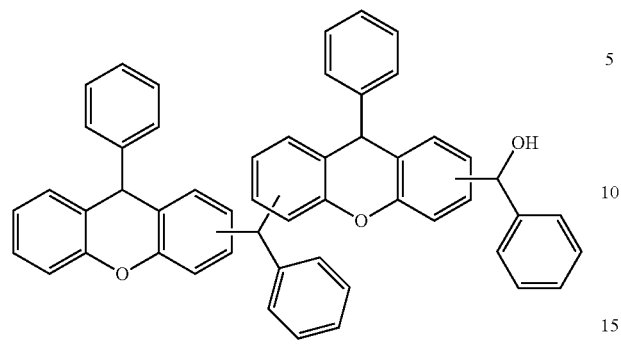
Chemical Formula 19a
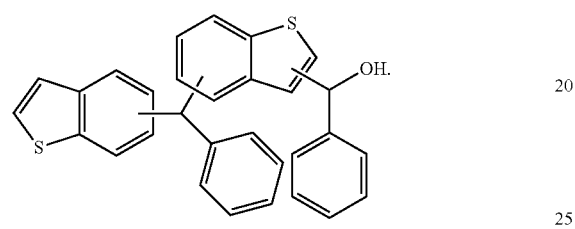
11. An organic layer provided by curing the organic layer composition as claimed in claim 10.
* * * * *